US00PP36602P3

(12) United States Plant Patent
Snijder

(10) Patent No.: US PP36,602 P3
(45) Date of Patent: Apr. 15, 2025

(54) ***PELARGONIUM* PLANT NAMED 'PEQZ0103'**

(50) Latin Name: ***Pelargonium* x interspecific**
Varietal Denomination: PEQZ0103

(71) Applicant: SYNGENTA CROP PROTECTION AG, Basel (CH)

(72) Inventor: Ronald Christiaan Snijder, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/220,336

(22) Filed: Jul. 11, 2023

(65) Prior Publication Data

US 2024/0224827 P1 Jul. 4, 2024

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324, 327
CPC . A01H 5/02; A01H 5/00; A01H 6/425; A01H 6/42
See application file for complete search history.

(56) References Cited

PUBLICATIONS

Fletcher. Colorful & Vibrant Annual Introductions for 2024 Part 2, Greenhouse Product News Jun. 2023, retrieved on Apr. 16, 2024 at https://www.nxtbook.com/greatamericanmediaservices/GPN/june-2023/index.php?startid=35#/p/32, 32-35. (Year: 2023).*
Syngenta Flowers Mojo Scarlet, retrieved on Apr. 16, 2024 at https://www.syngentaflowers-us.com/product/flower/70095951, 2 pp. (Year: 2024).*
YouTube video of Mojo Interspecific Geranium at CAST 2023, retrieved on Apr. 16, 2024 at https://www.youtube.com/watch?v=PxCB0_CHtOk, one page. (Year: 2023).*

* cited by examiner

*Primary Examiner* — June Hwu
(74) *Attorney, Agent, or Firm* — Dale Skalla

(57) ABSTRACT

A new *Pelargonium* plant named 'PEQZ0103' particularly distinguished by vivid orange red colored inflorescences with large semi-double florets, held above dark green foliage, on a vigorous upright-mounding plant.

1 Drawing Sheet

Latin name of the genus and species of the plant claimed: *Pelargonium* x interspecific.

Varietal denomination: 'PEQZ0103'.

BACKGROUND OF THE NEW PLANT

The present invention comprises a new *Pelargonium*, botanically known as *Pelargonium* interspecific, and hereinafter referred to by the variety name 'PEQZ0103'.

'PEQZ0103' is a product of a planned breeding program. The new cultivar 'PEQZ0103' has vivid orange red colored inflorescences with large semi-double florets, held above dark green foliage, on a vigorous upright-mounding plant.

'PEQZ0103' originates from a hybridization in a controlled breeding program made in July 2017 in a greenhouse in Enkhuizen, The Netherlands. The female parent was an unpatented plant of *P.* x interspecific parentage identified as 'PEZ-BC5047-01' with red florets, when compared to 'PEQZ0103'.

The male parent of 'PEQZ0103' was an unpatented, proprietary plant of *P.* x interspecific parentage, identified as 'PEZ-BC5032-05V' with lighter green foliage and purple florets when compared to 'PEQZ0103'. The resultant seed was sown in July 2017.

'PEQZ0103' was selected as one flowering plant within the progeny of the stated cross in May 2018 in a greenhouse in Enkhuizen, The Netherlands.

The first act of asexual reproduction of 'PEQZ0103' was accomplished when vegetative stem cuttings were propagated from the initial selection in June 2018 in a greenhouse in Enkhuizen, The Netherlands.

BRIEF SUMMARY OF INVENTION

Horticultural examination of plants grown from cuttings of the plant initiated in July 2018 in Enkhuizen, The Netherlands and continuing thereafter, has demonstrated that the combination of characteristics as herein disclosed for 'PEQZ0103' are firmly fixed and are retained through successive generations of asexual reproduction.

'PEQZ0103' has not been observed under all possible environmental conditions. The phenotype may vary significantly with variations in environment such as temperature, light intensity, and day length.

A Plant Breeder's Right for this cultivar was applied for in the European Union on Nov. 9, 2022, No. 2022/2509. 'PEQZ0103' has not been made publicly available prior to the effective filing date of this application, notwithstanding any disclosure that may have been made less than one year prior to the effective filing date of this application by the inventor or another who obtained 'PEQZ0103' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0103' with colors being as true as possible with an illustration of this type.

Figure 1:
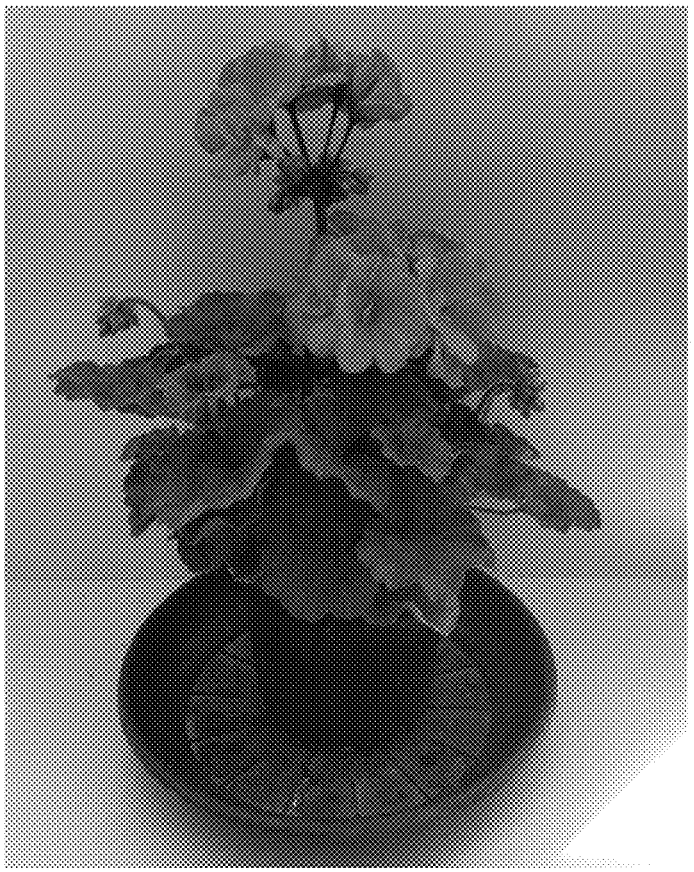
Figure 2:
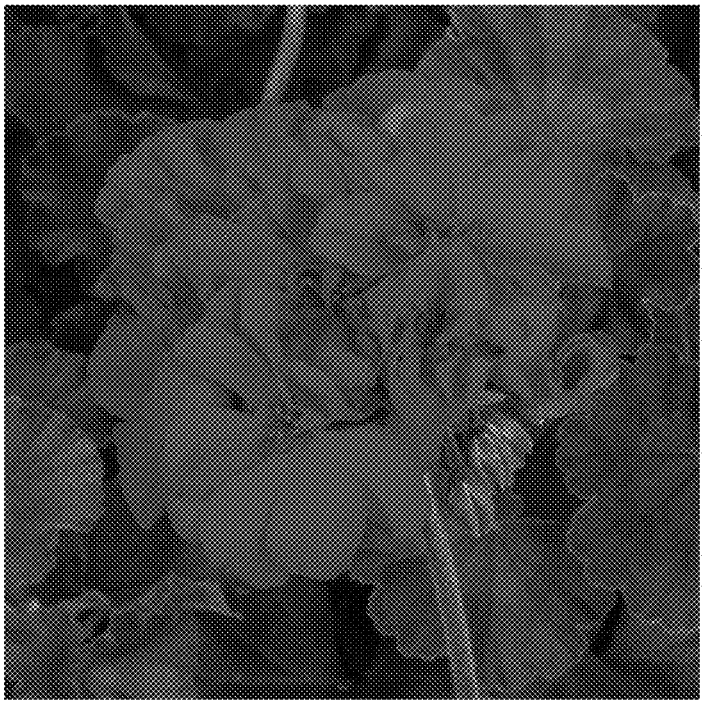

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early June 2022 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in June 2022.

Color references are made to The Royal Horticultural Society Colour Chart (R.H.S.) sixth edition, 2015.

TABLE 1

DIFFERENCES BETWEEN THE NEW VARIETY 'PEQZ0103' AND A MOST SIMILAR VARIETY

| | 'FISGRAND' (U.S. Plant Pat. No. 8,760, expired) | 'PEQZ0103' |
|---|---|---|
| Color of upper petals: | Vivid reddish orange, RHS 40A | Vivid reddish orange, slightly darker than RHS 33A |
| Color upper side of leaf: | Medium green, RHS 137C | Dark green, RHS 137A |

Plant:

*Form, growth and habit.*—Upright growth habit.
*Plant height.*—24-27 cm.
*Plant height (inflorescence included).*—30-33 cm.
*Plant width.*—18-22 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Variegation.*—Absent.
*Immature leaf, color upper surface.*—Closest to RHS 137B.
*Immature leaf, lower surface.*—Closest to RHS 138B.
*Mature leaf, color upper surface.*—Closest to RHS 137A.
*Mature leaf, color lower surface.*—Closest to RHS 138B.
*Length.*—5-6 cm.
*Width.*—8-9 cm.
*Shape.*—Cordate.
*Base shape.*—Cordate.
*Sinus of mature leaf.*—Narrow on young mature leaf, wider on older leaf.
*Leaf base openness.*—Variable, some leaves almost closed, some leaves open or slightly open.
*Apex shape.*—Acute.
*Margin.*—Slightly dentate.
*Texture upper side.*—Hirsute.
*Texture lower side.*—Hirsute.
*Leaf zonation color.*—RHS N189A.
*Leaf zonal intensity.*—Weak.
*Position.*—Middle.
*Size.*—Medium.
*Color of veins, upper surface.*—RHS 137A, largely indistinct.
*Color of veins, lower surface.*—RHS 144B, becoming indistinct.
*Pattern of veining.*—Palmate.
*Petiole color.*—RHS 143B.
*Petiole length.*—4-6 cm.
*Diameter of petiole.*—0.2 cm.
*Texture.*—Pilose, hirsute, glandular hairs.

Stem:

*Quantity of branches.*—5-9.
*Color of stem.*—Close to RHS 143B.
*Anthocyanin coloration of stem.*—Little to no anthocyanin coloration.
*Length of stem.*—9-20 cm.
*Diameter.*—0.5 cm.
*Length of internodes.*—1-4 cm.
*Texture.*—Sparsely hirsute, pilose, glandular hairs.

Peduncle:

*Color of peduncle.*—RHS 143C.
*Length of peduncle.*—13-18 cm.
*Peduncle diameter.*—0.3-0.5 cm.
*Texture.*—Hirsute, glandular hairs.
*Anthocyanin coloration of peduncle.*—Little to no anthocyanin coloration.

Pedicel:

*Color of pedicel.*—RHS 183B.
*Length of pedicel.*—2.2-2.4 cm.
*Diameter of pedicel.*—0.15 -0.2 cm.
*Texture.*—Sparsely pilose, glandular hairs.
*Pedicel swelling.*—Swelling was not observed.

Bud (just before opening):

*Color.*—RHS 44B.
*Length.*—1.2-1.4 cm.
*Width.*—0.5-0.6 cm.
*Shape.*—Elliptical.

Inflorescence:

*Type.*—Umbel; semi-spherical or nearly semi-spherical.
*Lastingness of individual flowers.*—7-9 days at 18° C. temperature.
*Number of inflorescences per plant.*—6-12, with 5-12 immature umbels in various stages.
*Average number of flowers per inflorescence.*—6.
*Average total number of buds.*—22.
*Fragrance.*—None.
*Umbel diameter.*—10-12 cm.
*Umbel depth.*—7-8 cm.

Corolla:

*Form.*—Semi-double.
*Number of petals.*—7-10, 2-4 petaloids.
*Diameter of flower.*—4.5-5 cm.
*Depth of flower.*—1-2 cm.
*Side view shape.*—Concave.
*Color upper petals, upper surface.*—Vivid reddish orange, slightly darker than RHS 33A.

*Color upper petals, lower surface*.—Vivid reddish orange, slightly darker than RHS 33A.
*Length of upper petals*.—2.5-2.9 cm.
*Width of upper petals*.—1.4-1.7 cm.
*Color lower petals, upper surface*.—Vivid reddish orange, slightly darker than RHS 33A.
*Color lower petals, lower surface*.—Vivid reddish orange, slightly darker than RHS 33A.
*Markings on upper petals*.—None.
*Markings on lower petals*.—None.
*Length of lower petals*.—2.2-2.5 cm.
*Width of lower petals*.—1.5-1.9 cm, petaloids variably smaller and with variable shape.
*Petal shape*.—Obovate to spathulate.
*Apex shape*.—Rounded.
*Margin*.—Entire.
*Base*.—Attenuate.
*Petal texture*.—Papillose on both surfaces.

Calyx:
*Number of sepals*.—5.
*Color of sepals*.—RHS 144A, mottling at base RHS 187B, increasing while ageing.
*Length of sepals*.—1-1.2 cm.
*Width of sepals*.—0.2-0.4 cm.
*Sepal shape*.—Lanceolate to linear.
*Apex shape*.—Acute.
*Margins*.—Mostly fused.
*Texture, upper surface*.—Glabrous.
*Lower surface*.—Glandular hairs, hirsute.
*Sepal flexing*.—Mostly unflexed sepals. The narrowest sepals might flex moderately.

Reproductive organs:
Gynoecium:
*Pistil*.—RHS 71A.
*Length*.—0.7 cm.
*Style color*.—RHS 71A.
*Style length*.—0.3 cm.
*Stigma color*.—RHS 71A.
*Ovary color*.—RHS 183A.
*Ovary length*.—0.4-0.5 cm.
*Ovary diameter*.—0.2 cm.

Androecium:
*Number of stamens*.—6-9 with 1-5 staminoids.
*Color of filaments*.—Base RHS N155A, apex RHS 52A.
*Length filaments*.—0.7 cm.
*Anther color*.—RHS 52B.
*Length of anthers*.—0.3 cm.
*Color of pollen*.—RHS N172A.
*Pollen amount*.—Scarce.
*Fertility/seed set*.—Has not been determined to date.
*Disease/pest resistance*.—Has not been determined to date.

What is claimed is:

1. A new and distinct variety of *Pelargonium* plant named 'PEQZ0103' substantially as illustrated and described herein.

* * * * *